(12) United States Patent
Stoessel et al.

(10) Patent No.: US 7,923,521 B2
(45) Date of Patent: Apr. 12, 2011

(54) PROCESS FOR PREPARING ORTHO-METALLATED METAL COMPOUNDS

(75) Inventors: Philipp Stoessel, Frankfurt am Main (DE); Rocco Fortte, Frankfurt (DE); Amir Parham, Frankfurt (DE); Esther Breuning, Niedernhausen (DE); Holger Heil, Darmstadt (DE); Horst Vestweber, Gilserberg (DE)

(73) Assignee: Merck Patent GmbH, Darmstadt (DE)

( * ) Notice: Subject to any disclaimer, the term of this patent is extended or adjusted under 35 U.S.C. 154(b) by 87 days.

(21) Appl. No.: 12/095,970

(22) PCT Filed: Nov. 9, 2006

(86) PCT No.: PCT/EP2006/010740
§ 371 (c)(1),
(2), (4) Date: Jun. 3, 2008

(87) PCT Pub. No.: WO2007/065523
PCT Pub. Date: Jun. 14, 2007

(65) Prior Publication Data
US 2008/0312396 A1 Dec. 18, 2008

(30) Foreign Application Priority Data
Dec. 5, 2005 (DE) .......................... 10 2005 057 963

(51) Int. Cl.
*C08G 79/00* (2006.01)

(52) U.S. Cl. ................. 528/9; 556/136; 556/137; 546/2; 546/4; 546/6; 546/110

(58) Field of Classification Search .................. 556/136, 556/137; 528/9; 546/2, 4, 6, 10
See application file for complete search history.

(56) References Cited

U.S. PATENT DOCUMENTS

| 4,539,507 | A | 9/1985 | VanSlyke et al. |
| 5,151,629 | A | 9/1992 | VanSlyke |
| 7,179,915 | B2 * | 2/2007 | Stossel et al. ................. 544/255 |
| 7,306,856 | B2 * | 12/2007 | Igarashi et al. ................ 428/690 |
| 2004/0077862 | A1 | 4/2004 | Stossel et al. |
| 2004/0138455 | A1 * | 7/2004 | Stossel et al. ..................... 546/2 |
| 2006/0142552 | A1 | 6/2006 | Bach et al. |
| 2006/0142604 | A1 | 6/2006 | Bach et al. |
| 2006/0252936 | A1 | 11/2006 | Stossel et al. |
| 2007/0034863 | A1 | 2/2007 | Fortte et al. |
| 2007/0080342 | A1 * | 4/2007 | Bold et al. ...................... 257/40 |
| 2007/0135635 | A1 | 6/2007 | Stössel et al. |

FOREIGN PATENT DOCUMENTS

| JP | 2004-238379 A | 8/2004 |
| WO | WO-02/060910 A1 | 8/2002 |
| WO | WO-2004/084326 A2 | 9/2004 |
| WO | WO-2004/085449 A1 | 10/2004 |
| WO | WO-2004/099223 A1 | 11/2004 |
| WO | WO-2004/108738 A1 | 12/2004 |
| WO | WO-2005/033244 A1 | 4/2005 |
| WO | WO-2005/042548 A1 | 5/2005 |

* cited by examiner

*Primary Examiner* — Milton I Cano
*Assistant Examiner* — Michael Leonard
(74) *Attorney, Agent, or Firm* — Connolly Bove Lodge & Hutz LLP

(57) ABSTRACT

The present invention describes a process for the preparation of homoleptic and heteroleptic tris-ortho-metallated metal compounds which are used as coloring components as functional materials in a number of different applications which can be ascribed to the electronics industry in the broadest sense.

17 Claims, No Drawings

PROCESS FOR PREPARING ORTHO-METALLATED METAL COMPOUNDS

RELATED APPLICATIONS

This application is National State of PCT/EP2006/010740, filed on Nov. 9, 2006, which claims foreign priority to German application 10 2005 057 963.6 filed on Dec. 5,2005.

The present invention describes a process for the preparation of homoleptic and heteroleptic tris-ortho-metallated metal compounds from simple starting compounds.

Organometallic compounds, especially compounds of the $d^8$ metals, are used as functional materials in a number of different applications which can be ascribed to the electronics industry in the broadest sense. The general structure of organic electroluminescent devices and their individual components, the organic light-emitting diodes (OLEDs), is described in U.S. Pat. No. 4,539,507 and U.S. Pat. No. 5,151,629. A development in this respect is the use of organometallic complexes which exhibit phosphorescence instead of fluorescence (M. A. Baldo et al, *Appl. Phys. Lett.* 1999, 75, 4-6). For spin-statistical reasons, an up to four-fold energy and power efficiency is possible using organometallic compounds. This development appears to be establishing itself over singlet emitters, at least for red and green emission.

For this purpose, efficient chemical-synthetic access to the corresponding, high-purity organometallic compounds must be possible. This is of crucial importance for resource-conserving utilisation of the said class of compounds, in particular taking into account the rarity of the late transition metals Rh, Ir, Pd and Pt.

Efficient access to correspondingly functionalised metal complexes is also necessary for use of corresponding metal complexes as monomers for the preparation of oligomers and polymers. This requires, in particular, suitable access to heteroleptic metal complexes which carry polymerisable groups on one or two of the ligands, while the third ligand is not functionalised by polymerisable groups.

Some processes for the preparation of tris-ortho-metallated organoiridium compounds are described in the literature. The synthetic routes, the yields and the characteristic properties of the syntheses are indicated briefly below with reference to the parent structure of the said class of compounds, tris[2-(2-pyridinyl-κN)phenyl-κC]iridium(III).

Starting from hydrated iridium(III) chloride and 2-phenylpyridine in a mixture of ethoxyethanol/water (3:1), fac-tris[2-(2-pyridinyl-κN)phenyl-κc]iridium(III) was obtained as by-product in a yield of approximately 10% after complex chromatographic purification methods, while the principal product obtained was the dimeric chloro-bridged iridium complex (K. A. King, P. J. Spellane, R. J. Watts, *J. Am. Chem. Soc.* 1985, 107, 1431-1432).

K. Dedeian et al. describe a process starting from iridium (III) tris(acetyl-acetonate) and 2-phenylpyridine by which fac-tris[2-(2-pyridinyl-κN)phenyl-κC]iridium(III) was obtained in a yield of 45%. In this process too, the product has to be purified from impurities by chromatographic methods, with halogenated hydrocarbons being used here (K. Dedeian, P. I. Djurovich, F. O. Garces, G. Carlson, R. J. Watts, *Inorg. Chem.* 1991, 30, 1685-1687).

In a further process, di-μ-chlorotetrakis[2-(2-pyridinyl-κN)phenyl-κC]diiridium(III), which is firstly prepared from hydrated iridium(III) chloride and 2-phenylpyridine in a yield of approximately 72% (S. Spouse, K. A. King, P. J. Spellane, R. J. Watts, *J. Am. Chem. Soc.* 1984, 106, 6647-6653), is used as starting material. This is reacted with 2-phenylpyridine and twice the molar amount of silver trifluoromethylsulfonate, based on the di-μ-chlorotetrakis[2-(2-pyridinyl-κN)phenyl-κC]diiridium (III). After chromatographic purification, the authors obtain fac-tris[2-(2-pyridinyl-κN)phenyl-κC]iridium(III) in a yield of 75% (M. G. Colombo, T. C. Brunold, T. Riedener, H. U. Güdel, *Inorg. Chem.* 1994, 33, 545-550). Besides the chromatographic purification, which is again carried out using halogenated hydro-carbons, the use of silver trifluoromethylsulfonate is disadvantageous since traces of silver are very difficult to remove from the product and have an adverse effect on the opto-electronic properties of the iridium complexes.

The synthesis of facial and meridional tris[2-(2-pyridinyl-κN)phenyl-κC]-iridium(III) was described by M. Thompson et al (A. B. Tamayo, B. D. Alleyne, P. I. Djurovich, S. Lamansky, I. Tsyba, N. N. Ho, M. E. Thompson, *J. Am. Chem. Soc.* 2003, 125, 7377-7387). To this end, di-μ-chloro-tetrakis[2-(2-pyridinyl-κN)phenyl-κC]diiridium(III) is heated with phenyl-pyridine in glycerol with addition of potassium carbonate A reaction temperature of approximately 200° C. gives the facial iridium complex, while a reaction temperature of 140-145° C. gives the meridional iridium complex. The yield in both cases is between 65 and 80%. In both cases, product mixtures are formed from which the pure complexes have to be isolated by chromatography, meaning that this process is not suitable for industrial use.

The process described in WO 02/060910 consists in the reaction of iridium(III) tris(acetylacetonate) and similar 1,3-ketoketonate complexes with an arylpyridine or heteroarylpyridine compound in the presence of a dipolar protic solvent with strong heating for extended reaction times (>20 h). Very good yields (up to 96%) and likewise very good purities (>99.9%) are obtained here. However, it is disadvantageous that this synthesis has to start from iridium(III) tris (acetylacetonate), which firstly has to be prepared from iridium chloride in a separate synthetic step. The yields cited in the literature for the preparation of iridium(III) tris(acetylacetonate) are in the order of only 25%, meaning that a considerable loss of iridium occurs here overall. The same applies to the process in accordance with WO 04/085449, which starts from heteroleptic iridium complexes which carry two ligands of the acetylacetonate type and two further ligands of the halide type. Here too, the ortho-metallated metal complexes are obtained in high yield and purity, but the iridium starting complexes have to be synthesised in a separate step, which again results in losses of yield. Furthermore, the two processes are not suitable for the preparation of heteroleptic metal complexes.

WO 04/099223 describes a process for the preparation of tris-ortho-metallated iridium complexes by reaction of the ligand with iridium halide in the presence of a silver, mercury, aluminum or antimony salt. As already described above, the use of metal salts, in particular silver salts, is disadvantageous since traces of metal are very difficult to remove from the product and have an adverse effect on the opto-electronic properties of the iridium complexes. The same also applies to the use of mercury, antimony other metals. The use of mercury salts is furthermore associated with a considerable health and environmental risk.

WO 04/084326 describes a process for the preparation of tris-ortho-metallated iridium complexes by reaction of $[L_2IrHal]_2$ with a further ligand of the arylpyridine type in the presence of an auxiliary ligand which is capable of breaking the metal-halogen bond. Auxiliary ligands described are, in particular, pyridines, triarylphosphines and ketoketonates. The synthesis can also be carried out in two steps in a one-pot process starting from the metal halide. The solvents used are protic solvents, in particular ethylene glycol, and the reaction is carried out under reflux (in ethylene glycol, i.e. at about 197° C.). Over two steps, starting from IrCl₃, a yield of 60% is obtained. An improvement in the yield would also be desirable here. This process furthermore has the disadvantage that it is carried out under drastic conditions (refluxing at 197° C. for 3 days). In the case of sensitive ligands, this may already result in decomposition of the ligand or the complex formed. Furthermore, the reaction conditions are unsuitable for the synthesis of tris-ortho-metallated heteroleptic metal complexes since ligand exchange always takes place under these reaction conditions, meaning that it is not possible to isolate uniform heteroleptic tris-ortho-metallated complexes, but instead only complex mixtures.

WO 05/042548 describes a process for the synthesis of heteroleptic iridium complexes by reaction of [L₂IrHal]₂ with an organometallic derivative, in particular an alkali or alkaline earth metal derivative, of an arylpyridine ligand. Good yields of above 95% are obtained here (starting from [L₂IrHal]₂). However, this process has the disadvantage that it proceeds via an alkali or alkaline earth metal derivative as intermediate, which is air- and water-sensitive, meaning that the reaction has to be carried out with particular precautionary measures, which may mean a safety risk, in particular on an industrial scale. This method does not represent an advantage for the preparation of homoleptic complexes since the reaction is carried out via two steps and since the intermediate, [L₂IrHal]₂, has to be prepared, isolated and purified in a separate step. A further disadvantage is that the ligand precursors required for this process can often only be prepared in a complex manner or are virtually inaccessible synthetically and that the corresponding organometallic derivative of the ligand does not form selectively in some cases.

JP 2004/238379 describes a process for the synthesis of iridium complexes by reaction of [L₂IrHal]₂ with a further ligand in the presence of a base. The base used is preferably an inorganic base, an alkali metal alkoxide or an organic amine. The solvents indicated are polar solvents, in particular ethylene glycol, glycerol, 2-methoxyethanol, 2-ethoxyethanol and DMF. The only working example describes the synthesis using triethanol-amine as base in ethylene glycol with use of microwave radiation.

As evident from the literature mentioned above, it would be advantageous to have available a broadly applicable process by means of which tris-ortho-metallated iridium complexes can be synthesised simply, in high yield and under mild reaction conditions from readily accessible iridium(III) halide. Significant improvements over the prior art are still necessary, in particular, for the synthesis of heteroleptic metal complexes. It would furthermore be advantageous to have available a simple and reproducible process for the preparation of meridional complexes. These complexes are only accessible with difficulty using the processes in accordance with the prior art since they are thermodynamically unstable relative to the corresponding facial complexes.

Surprisingly, it has been found that the synthesis of tris-ortho-metallated rhodium and iridium complexes and bis-ortho-metallated palladium and platinum complexes starting from metal halides or halide-bridged dimeric complexes proceeds under particularly mild conditions and gives particularly good yields if the reaction is carried out in the presence of a salt whose anion contains at least two oxygen atoms, in a solvent mixture comprising an organic solvent and at least 5% by vol. of water. This process enables both the facial and also the meridional iridium complexes, which are otherwise only accessible with difficulty, to be obtained selectively, depending on the choice of salt added. The meridional complexes can also be converted into the corresponding facial complexes in a subsequent step. This is thus the first process, which leads from readily accessible hydrated iridium halide to tris-ortho-metallated iridium complexes in one step under mild reaction conditions and in good yields. This result is particularly surprising since it is known from the literature that on the one hand the use of a mixture of ethoxyethanol and water only results in yields in the order of 10% and that on the other hand the use of a purely organic solvent together with a base requires drastic reaction conditions (activation by the use of microwave radiation) in order to achieve high yields. It is therefore not obvious that the combination of a solvent system comprising an organic solvent and water together with certain salts has such a strong influence on the course of the reaction. It has furthermore been found that the process can be used not only for the synthesis of iridium complexes, but also for the synthesis of corresponding rhodium, palladium and platinum complexes.

The invention relates to a process for the preparation of metal complexes of the formula (1)

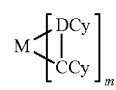

Formula (1)

in which:

M is Rh, Ir, Pd or Pt,

DCy is on each occurrence, identically or differently, a cyclic group which contains at least one neutral donor atom, preferably nitrogen or phosphorus, via which the cyclic group is bonded to the metal and which may carry one or more substituents R; the groups DCy and CCy are connected to one another via a covalent bond; in addition, they may furthermore be connected to one another via a radical R;

CCy is on each occurrence, identically or differently, a cyclic group which contains a carbon atom or a negatively charged nitrogen atom via which the cyclic group is bonded to the metal and which may carry one or more substituents R;

R is on each occurrence, identically or differently, F, Cl, Br, I, NO₂, CN, NH₂, NHR¹, N(R¹)₂, B(OH)₂, B(OR¹)₂, CHO, COOH, CON(R¹)₂, SO₃H, C(=O)R¹, P(=O)(R¹)₂, S(=O)R¹, S(=O)₂R¹, P(R¹)₃⁺, N(R¹)₃⁺, OH, SH, a straight-chain alkyl or alkoxy group having 1 to 20 C atoms or a branched or cyclic alkyl or alkoxy group having 3 to 20 C atoms, in each of which one or more non-adjacent CH₂ groups may be replaced by —O—, —S—, —NR¹—, —CONR¹—, —CO—O—, —CR¹=CR¹— or —C≡C— and which may also be substituted by one or more groups R², or an aromatic or heteroaromatic ring system having 5 to 30 aromatic ring atoms, which may be substituted by one or more radicals R², or an aryloxy, heteroaryloxy, arylamino or heteroarylamino group having 5 to 30 aromatic ring atoms, which may be substituted by one or more radicals R²; two or more substituents R here, both on the same ring and also on the two different rings together, may in turn define a further mono- or polycyclic, aliphatic or aromatic ring system with one another or with R¹, R² and/or R³;

R¹ is on each occurrence, identically or differently, H, a straight-chain alkyl group having 1 to 20 C atoms or a branched or cyclic alkyl group having 3 to 20 C atoms, in each of which one or more non-adjacent CH$_2$ groups which are not bonded directly to a heteroatom may be replaced by —O—, —S—, —NR$^3$—, —CONR$^3$—, —CO—O—, —CR$^3$=CR$^3$— or —C≡C— and which may also be substituted by one or more groups R$^2$, or an aromatic or heteroaromatic ring system having 5 to 30 aromatic ring atoms, which may be substituted by one or more radicals R$^2$; two or more substituents R$^1$ here may in turn define a further mono- or polycyclic, aliphatic or aromatic ring system with one another or with R, R$^2$ and/or R$^3$;

R$^2$ is on each occurrence, identically or differently, H, F, Cl, Br, I, NO$_2$, CN, NH$_2$, NHR$^3$, N(R$^3$)$_2$, B(OH)$_2$, B(OR$^3$)$_2$, CHO, COOH, CON(R$^3$)$_2$, SO$_3$H, C(=O)R$^1$, P(=O)(R$^1$)$_2$, S(=O)R$^1$, S(=O)$_2$R$^1$, P(R$^3$)$_3$$^+$, N(R$^3$)$_3$$^+$, OH, SH, a straight-chain alkyl or alkoxy group having 1 to 20 C atoms or a branched or cyclic alkyl or alkoxy group having 3 to 20 C atoms, in each of which one or more non-adjacent CH$_2$ groups may be replaced by —O—, —S—, —NR$^3$—, —CONR$^3$—, —CO—O—, —CR$^3$=CR$^3$— or —C≡C— and which may also be substituted by one or more groups R$^3$, or an aromatic or heteroaromatic ring system having 5 to 30 aromatic ring atoms, which may be substituted by one or more radicals R$^3$, or an aryloxy, heteroaryloxy, arylamino or heteroarylamino group having 5 to 30 aromatic ring atoms, which may be substituted by one or more radicals R$^3$; two or more substituents R$^2$ here, both on the same ring and also on the two different rings together, may in turn define a further mono- or polycyclic, aliphatic or aromatic ring system with one another or with R, R$^1$ and/or R$^3$;

R$^3$ is, identically or differently on each occurrence, H or an aliphatic or aromatic hydrocarbon radical having 1 to 20 C atoms; two or more radicals R$^3$ here may also form a ring system with one another;

m is 2 for M=Pd or Pt and is 3 for M=Rh or Ir;

by reaction of a metal compound of the formula (2), of the formula (3) or of the formula (4)

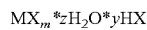   Formula (2)

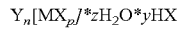   Formula (3)

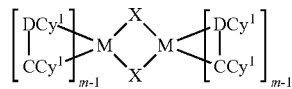   Formula (4)

where M and m have the same meaning as described for formula (1), and the following applies to the other symbols and indices.

x is on each occurrence, identically or differently, F, Cl, Br or I;

Y is on each occurrence, identically or differently, an alkali metal cation, an alkaline earth metal cation, an ammonium cation, a tetraalkylammonium cation having 4 to 40 C atoms or a tetraalkylphosphonium cation having 4 to 40 C atoms;

P is 4 for M=Pd or Pt and is 6 for M=Rh or Ir;

n corresponds to the charge of M for a monovalent cation Y and corresponds to half the charge of M for a divalent cation Y;

z is 0 to 100;

y is 0 to 100;

with a compound of the formula (5)

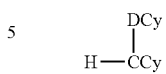   Formula (5)

in which DCy and CCy have the meanings mentioned under formula (1), characterised in that the reaction is carried out in the presence of a salt whose anion contains at least two oxygen atoms, in a solvent mixture comprising at least one organic solvent and at least 2% by vol. of water.

For the purposes of this invention, cyclic means both monocyclic and also bicyclic or polycyclic.

If the radicals form a ring system with one another, fused aromatic or non-aromatic systems can be formed therefrom. It should explicitly be emphasised again here that radicals which are bonded to different groups, for example to CCy and DCy, can also form a ring system with one another.

For the purposes of the present invention, a C$_1$- to C$_{40}$-alkyl group, in which, in addition, individual H atoms or CH$_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, adamantyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A C$_1$- to C$_{40}$-alkoxy group is particularly preferably taken to mean methoxy, ethoxy, n-propoxy, i-propoxy, n-butoxy, i-butoxy, s-butoxy, t-butoxy or 2-methylbutoxy. An aromatic or heteroaromatic ring system having 1 to 30 aromatic ring atoms, which may also be substituted by the above-mentioned radicals R$^2$ or R$^3$ and which may be linked to the aromatic or heteroaromatic system via any desired positions, is taken to mean, in particular, groups derived from benzene, naphthalene, anthracene, phenanthrene, pyrene, chrysene, perylene, fluoranthene, tetracene, pentacene, benzopyrene, biphenyl, biphenylene, terphenyl, terphenylene, fluorene, spirobifluorene, truxene, isotruxene, dihydrophenanthrene, dihydropyrene, tetrahydropyrene, cis- or trans-indenofluorene, furan, benzofuran, iso-benzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Depending on the starting materials and ligands, both homoleptic and also heteroleptic metal complexes can be synthesised. A homoleptic complex is taken to mean a compound in which only identical ligands are bonded to a metal. Heteroleptic complexes are those in which different ligands are bonded to the metal. This relates both to ligands having a different ligand basic structure and also to ligands which have the same basic structure, but are differently substituted. If a compound of the formula (2) or a compound of the formula (3) is reacted with a compound of the formula (5), homoleptic metal complexes are generally formed. If a compound of the formula (4) is reacted with a ligand of the formula (5) of the same type, homoleptic metal complexes are likewise generally formed. If a compound of the formula (4) is reacted with a ligand of the formula (5) of a different type, heteroleptic metal complexes are formed. Preferred octahedral heteroleptic metal complexes are those which contain two identical ligands and a third different ligand.

Both facial and also meridional octahedral complexes are accessible selectively by the process according to the invention, depending on the way in which the reaction is carried out.

Facial or meridional coordination in the sense of this application describes the octahedral environment of the metal M with the six donor atoms. Facial coordination is present if three identical donor atoms occupy a triangular face in the (pseudo)octahedral coordination polyhedron and three identical donor atoms, but which are different from the first donor atoms, occupy another triangular face in the (pseudo)octahedral coordination polyhedron. In the case of meridional coordination, three identical donor atoms occupy the first meridian in the (pseudo)octahedral coordination polyhedron and three identical donor atoms, but which are different from the first donor atoms, occupy the other meridian in the (pseudo) octahedral coordination polyhedron. This is shown below with reference to the example of coordination of three N donor atoms and three C donor atoms (scheme 1). Since this definition relates to donor atoms and not to the rings CCy and DCy which provide these donor atoms, the three rings CCy and the three rings DCy may be identical or different on each occurrence and nevertheless correspond to facial or meridional coordination in the sense of this application. Identical donor atoms are taken to mean those which consist of the same elements (for example carbon or nitrogen), irrespective of whether these elements are incorporated into different structures. This definition can likewise be applied to metal complexes which generally contain three neutral and three anionic coordinating atoms, meaning that this definition can also be used if, for example, a ligand coordinates via a neutral nitrogen atom and an anionic nitrogen atom.

Scheme 1:

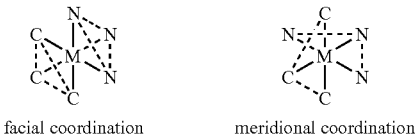

facial coordination   meridional coordination

Preferred metal starting materials according to the invention are those in which the symbol M stands for iridium or platinum, in particular for iridium.

Preferred compounds of the formula (2) are those in which the index z stands for 1 to 10, particularly preferably 1 to 3. Preferred compounds of the formula (2) are furthermore those in which the index y stands for 0 to 10, particularly preferably 0 to 3.

Preferred compounds of the formula (3) are those in which the index z stands for 0 to 10, particularly preferably 0 to 3. Preferred compounds of the formula (3) are furthermore those in which the index y stands for 0 to 10, particularly preferably 0 to 3, very particularly preferably 0.

The indices z and y here do not have to be integers since the complexes may also contain non-stoichiometric amounts of water and HX. The water content in particular can vary depending on the batch since hygroscopic metal salts are involved. However, the proportion of water in the starting material has no effect on the reaction since a relatively large amount of water is added to the reaction mixture.

Preferred metal starting materials of the formulae (2), (3) and (4) are furthermore those in which the symbol X, identically or differently on each occurrence, stands for chlorine or bromine, particularly preferably for chlorine.

Preferred ligands are those in which the symbol CCy, identically or differently on each occurrence, stands for an aromatic or heteroaromatic group which has 5 to 20 aromatic ring atoms and which may carry one or more substituents R. The aromatic or heteroaromatic group CCy may also be fused. The uncoordinated ligand here in at least one ortho-position to the bond from DCy must have an unsubstituted carbon atom or an NH group, which can then bond to the metal. The group CCy particularly preferably bonds to the metal via a carbon atom. Preferred aromatic groups CCy are those having 6 to 20 C atoms, preferably 6 to 14 C atoms, particularly preferably 6 or 10 C atoms, which may also be substituted by one or more radicals R. Very particularly preferred aromatic groups are phenyl, naphthyl, anthryl, fluorenyl and phenanthrenyl, in particular phenyl and naphthyl, each of which may be substituted by one or more radicals R. Preferred heteroaromatic groups CCy are those having at least one heteroatom and at least two C atoms, where the sum of heteroatoms and C atoms must be at least 5. The heteroatoms are preferably selected from N, S and/or O. Preferred heteroaromatic groups contain 5 to 14 aromatic ring atoms, particularly preferably 5, 6, 9 or 10 aromatic ring atoms. Particularly preferred heteroaromatic groups are derived from thiophene, pyrrole, furan, imidazole, pyrazole, pyridine, pyrazine, pyrimidine, pyridazine, benzothiophene, indole, carbazole, benzofuran, quinoline, isoquinoline or quinoxaline, each of which may be substituted by one or more radicals R.

Preferred ligands are furthermore those in which the symbol DCy, identically or differently on each occurrence, stands for a cyclic group having 5 to 20 ring atoms which contains a neutral nitrogen atom in the ortho-position to the bond from CCy as donor atom. The nitrogen here is preferably either bonded in an imine functionality or is part of a heteroaromatic system. The DCy ring system contains at least one nitrogen atom and at least two carbon atoms, where the sum of all heteroatoms and carbon atoms must be at least 5. DCy preferably contains 5 to 20 aromatic ring atoms, particularly preferably 5 to 14 aromatic ring atoms, very particularly preferably 5, 6, 9 or 10 aromatic ring atoms. Particularly preferred ring systems DCy are selected from pyridine, quinoline, isoquinoline, quinoxaline, benzopyrimidine, 2-azaanthracene, phenanthridine, oxazole, thiazole, benzoxazole or benzothiazole, in particular pyridine, quinoline, isoquinoline or benzopyrimidine, each of which may be substituted by one or more radicals R.

The reaction is carried out with addition of a salt which contains at least two oxygen atoms. The salt here can be either an organic salt or an inorganic salt. Zwitterionic compounds (so-called internal salts) are also salts for the purposes of this invention and are suitable for the process according to the invention. At least one of the oxygen atoms is preferably negatively charged. The oxygen atoms are furthermore preferably bonded in the salt in a 1,3-, 1,4- or 1,5-arrangement (scheme 2, where bonding to central atoms other than carbon is also possible, for example to sulfur, nitrogen or phosphorus), i.e. they preferably bond to the same central atom (1,3-arrangement), to adjacent central atoms (1,4-arrangement) or in each case to the next central atom but one (1,5-arrangement). The oxygen atoms are particularly preferably bonded in the salt in the 1,3- or 1,4-arrangement, very particularly preferably in the 1,3-arrangement. It is also possible for the salt to be formed in situ by addition of a base.

Scheme 2:

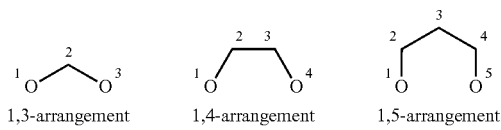

1,3-arrangement    1,4-arrangement    1,5-arrangement

For the purposes of this invention, an internal salt or a zwitterion is taken to mean a compound which contains at least one anionic group containing at least two oxygen atoms and which contains at least one cationic group in the same molecule. An internal salt of this type can be formed, for example, by intramolecular acid-base reaction between an acid group and a basic group in the same molecule, for example between a carboxylic acid group and an amino group in an aminocarboxylic acid.

Preferred inorganic salts are alkali metal, alkaline earth metal, ammonium, tetraalkylammonium, tetraalkylphosphonium and/or tetraarylphosphonium salts of carbonate, hydrogencarbonate, sulfate, hydrogensulfate, sulfite, hydrogensulfite, nitrate, nitrite, phosphate, hydrogenphosphate, dihydrogenphosphate, borate, in particular the alkali metal, ammonium and tetraalkylammonium salts. In all these salts, the oxygen atoms are bonded in a 1,3-arrangement.

Preferred organic salts are the alkali metal, alkaline earth metal, ammonium, tetraalkylammonium, tetraalkylphosphonium and/or tetraarylphosphonium salts of organic carboxylic acids having 1 to 20 C atoms, in particular formate, acetate, fluoroacetate, trifluoroacetate, trichloroacetate, propionate, butyrate, oxalate, benzoate, pyridinecarboxylate, of organic sulfonic acids having 1 to 20 C atoms, in particular $MeSO_3^-$, $EtSO_3^-$, $PrSO_3^-$, $F_3CSO_3^-$, $C_4F_9SO_3^-$, phenyl-$SO_3^-$, ortho-, meta- or para-tolyl-$SO_3^-$, and of α-ketocarboxylates, such as, for example, salts of pyruvic acid, β-ketoketonates, in particular acetyl acetonate, β-ketocarboxylates, such as, for example, salts of β-ketobutyric acid, and salts of pyrocatechol and salicylic acid, in particular in each case those having up to 20 C atoms. The oxygen atoms in the salts of organic carboxylic acids and organic sulfonic acids are bonded in a 1,3-arrangement, those in oxalate are bonded both in a 1,3- and in a 1,4-arrangement, those in β-ketoketonates are bonded in a 1,5-arrangement and those in β-ketocarboxylates are bonded in a 1,3- and in a 1,5-arrangement.

The carboxylates and sulfonates here can have a linear, branched or cyclic basic structure and can be aliphatic and/or aromatic. They may furthermore be substituted by the above-defined groups R or unsubstituted.

Alkali metal salts are taken to mean lithium, sodium, potassium, rubidium and caesium salts, preferably sodium and potassium salts. Alkaline earth metal salts are taken to mean beryllium, magnesium, calcium, strontium and barium salts, preferably magnesium salts. Tetraalkylammonium salts are preferably taken to mean those having a total of 4 to 40 C atoms, in particular tetramethylammonium, tetraethylammonium, tetrapropylammonium and tetrabutylammonium. Tetraalkylphosphonium salts are preferably taken to mean those having a total of 4 to 40 C atoms, in particular tetramethylphosphonium, tetraethylphosphonium, tetrapropylphosphonium and tetrabutylphosphonium. Tetraarylphosphonium salts are preferably taken to mean those having a total of 20 to 40 C atoms, in particular tetraphenyl-phosphonium and tetratolylphosphonium. Use is predominantly made here of salts which are soluble in the reaction medium, preferably those which are soluble in a concentration of at least 0.001 mol/l, particularly preferably in a concentration of at least 0.01 mol/l, very particularly preferably in a concentration of at least 0.1 mol/l.

Preferred internal salts are aminocarboxylic acids, preferably having 2 to 20 C atoms, which are predominantly in zwitterionic form in neutral medium, in particular α-amino acids, such as glycine, alanine, arginine, asparagine, aspartic acid, glutamine, glutamic acid, histidine, leucine, isoleucine, lysine, phenylalanine, proline, serine, threonine, tryptophan, tyrosine or valine, likewise β- and γ-amino acids, such as γ-aminobutyric acid, aromatic amino acids, such as 2-aminobenzoic acid, 3-aminobenzoic acid, 4-aminobenzoic acid, polyaminocarboxylic acids, such as EDTA and derivatives of EDTA, and the corresponding N-alkylated aminocarboxylic acids of the above-mentioned classes of compound, where the alkyl groups preferably contain 1 to 10 C atoms, particularly preferably 1, 2, 3 or 4 C atoms, such as, for example, N,N-dimethylglycine, N,N-diethylglycine, N,N-dimethylalanine, 4-N,N-dimethylaminobutyric acid, etc. Preferred internal salts are furthermore aminosulfonic acids, preferably having 2 to 20 C atoms, such as, for example, taurine, and the corresponding N-alkylated aminosulfonic acids, where the alkyl groups preferably contain 1 to 10 C atoms, particularly preferably 1, 2, 3 or 4 C atoms. Preference is furthermore given to the salts of these amino acids or aminosulfonic acids which are obtained by abstraction of one or more protons from these compounds, where suitable cations are the above-mentioned cations.

The preferred molar ratio of metal to the added salt is 1:1 to 1:1000, particularly preferably 1:5 to 1:300, very particularly preferably 1:10 to 1:150. The molar ratio of the metal compound of the formula (2) or formula (3) to the added salt is therefore preferably 1:1 to 1:1000, particularly preferably 1:5 to 1:300, very particularly preferably 1:10 to 1:150, and the molar ratio of the metal compound of the formula (4) to the added salt is preferably 1:2 to 1:2000, particularly preferably 1:10 to 1:600, very particularly preferably 1:20 to 1:300.

In accordance with the invention, the reaction is carried out in a solvent mixture comprising an organic solvent and water, preferably in homogeneous solution. Homogeneous here relates to the solvent mixture, the starting materials and the added salt, but not to the reaction product, which generally precipitates from the reaction mixture. Preference is therefore given to organic solvents which are miscible with water, in particular those which are miscible with water in any desired ratio. These are, in particular, polar protic and polar aprotic solvents.

Preferred polar protic solvents are alcohols, in particular alcohols having 1 to 5 C atoms, for example methanol, ethanol, n-propanol, isopropanol, n-butanol, isobutanol or tert-butanol, or also diols or polyalcohols, for example ethylene glycol, propylene glycol, glycerol, polyethylene glycols, for example PEG600 and PEG1000, and alkoxy alcohols, for example methoxy ethanol or ethoxy ethanol.

Preferred polar aprotic solvents are water-miscible open-chain ethers, for example triethylene glycol dimethyl ether, poly(ethylene glycol) dimethyl ether, water-miscible cyclic ethers, such as dioxane or THF, and DMSO, NMP and DMF.

The organic solvent used is particularly preferably a polar aprotic solvent, very particularly preferably a cyclic water-miscible ether, in particular dioxane.

In accordance with the invention, the proportion of water in the reaction medium is at least 2% by vol. The proportion of water is preferably in the range from 5 to 90% by vol., particularly preferably in the range from 7 to 75% by vol., very particularly preferably in the range from 10 to 60% by vol. A water content of 40 to 60% by vol. is particularly suitable.

The reaction is preferably carried out at a temperature in the range from 20 to 250° C., particularly preferably from 40 to 150° C., very particularly preferably from 50 to 100° C. These reaction conditions, which are significantly milder than the reaction conditions in accordance with the prior art, offer the advantage that the reaction can also be carried out with thermally and/or chemically sensitive ligands and that ligand-exchange reactions do not occur at these temperatures, meaning that heteroleptic complexes are also accessible in high yield, selectivity and purity by means of this process. Depending on the solvent mixture, the reaction can be carried out at these temperatures under reflux. Thus, the reaction in a mixture of dioxane and water is preferably carried out under reflux. In the case of a 1:1 mixture, this corresponds to a temperature of about 85-90° C. The reaction can also be carried out under pressure, for example in an autoclave.

The concentration of the metal starting compound of the formula (2) or formula (3) is preferably in the range from 0.5 mmol/l to 100 mmol/l, particularly preferably in the range from 1 to 30 mmol/l, very particularly preferably in the range from 2 to 10 mmol/l. The concentration of the metal starting compound of the formula (4) is preferably in the range from 1 to 1000 mmol/l, particularly preferably in the range from 5 to 500 mmol/l, very particularly preferably in the range from 10 to 100 mmol/l.

The preferred molar ratio of the metal compound of the formula (2) or formula (3) to the ligand of the formula (5) is 1:1 to 1:60, particularly preferably 1:3 to 1:10, very particularly preferably 1:3 to 1:8. The preferred molar ratio of the metal compound of the formula (4) to the ligand of the formula (5) is 1:1 to 1:100, particularly preferably 1:2 to 1:70, very particularly preferably 1:2 to 1:50.

Since the ligand is usually employed in excess, in some cases even in considerable excess, it may be appropriate, in particular in the case of ligands which are complex to synthesise, to recover the latter after the reaction. This can be carried out, for example, by extraction of the mother liquor with a water-immiscible solvent.

The reaction is preferably carried out over the course of 1 to 100 h, particularly preferably over the course of 5 to 50 h. It is evident that the reaction proceeds significantly more quickly than reactions in accordance with the prior art, in spite of the milder reaction conditions.

A further acceleration of the reaction can be achieved, for example, on use of microwave radiation. The way in which ortho-metallation reactions can generally be carried out in a microwave is described, for example, in WO 04/108738. However, the use of microwave radiation is not absolutely necessary in the process according to the invention in order to achieve good yields.

The process according to the invention enables the selective preparation of the facial or meridional metal complexes. It has been found here that the meridional metal complexes are formed, in particular, on use of metal carboxylates, for example acetate, while the corresponding facial metal complexes are formed on use of amino acids, alkylated amino acids, aminosulfonic acids, alkylated aminosulfonic acids and purely inorganic salts.

Preference is furthermore given to a process for the preparation of a facial tris-ortho-metallated metal complex of the formula (1), characterised in that firstly a meridional complex is prepared by a process according to the invention in accordance with the above description, followed by a reaction step for conversion of the meridional isomer into the facial isomer of the complex. This conversion of the meridional isomer into the facial isomer can be carried out by the input of energy, in particular thermal energy or electromagnetic radiation (UV radiation, microwave radiation, etc.). The conversion step here can be carried out either directly in the reaction solution after the reaction as a one-pot process, or it can be carried out in a separate reaction step after isolation of the meridional metal complex. The way in which the conversion of the meridional complex into the facial complex can be carried out is described, for example, by Thompson et al. (A. B. Tamayo, B. D. Alleyne, P. I. Djurovich, S. Lamansky, I. Tsyba, N. N. Ho, M. E. Thompson, *J. Am. Chem. Soc.* 2003, 125, 7377-7387).

The invention furthermore relates to the use of the process for the preparation of difunctionalised metal complexes, in particular for the preparation of dibromo compounds. These are particularly suitable for use as monomers for the preparation of polymers. The process according to the invention makes these monomers readily accessible with a wide range of ligands for the first time.

Since the process according to the invention gives access to heteroleptic metal complexes particularly simply, selectively and in good yields, for example octahedral complexes which are substituted by bromine, boronic acid or boronic acid esters, for example boronic acid glycol ester or boronic acid pinacol ester, as polymerisable functional group on two of the three ligands and carry no polymerisable group on the third ligand, polymers, oligomers or dendrimers of this type are likewise more readily accessible than in accordance with the prior art. The invention therefore furthermore relates to the use of difunctionalised compounds of the formula (1), obtained by a process according to the invention, for the preparation of conjugated, partially conjugated or non-conjugated polymers, oligomers or dendrimers. The functional groups of the difunctionalised compounds here are preferably halogen, in particular bromine, or boronic acid or boronic acid derivatives.

The process according to the invention offers the following advantages over the prior art:

1. The process according to the invention enables access to tris-ortho-metallated metal complexes from readily accessible metal halide in one step and in very good yield, while the processes in accordance with the prior art start from more complex starting materials, for example various metal ketoketonate complexes, or have significantly worse yields.
2. A further advantage of the process according to the invention are the mild reaction conditions. This is surprising since similar processes in accordance with the prior art which proceed with addition of acetyl acetonate or inorganic bases, such as hydrogen carbonate, but do not contain water in the reaction mixture proceed under significantly more drastic reaction conditions (use of microwave radiation, reaction at above 190° C.). This effect of water on the reaction is a surprising and unforeseeable result since in a reaction in a mixture of ethoxy-ethanol and water without addition of a salt in the prior art, a yield of only 10% was obtained.
3. The mild reaction conditions enable the process also to be utilised for the synthesis of metal complexes having thermally and/or chemically sensitive ligands which result in undesired side reactions in processes in accordance with the prior art.
4. The mild reaction conditions enable the selective synthesis of heteroleptic metal complexes. These are difficult to synthesise in accordance with the prior art since ligand-exchange reactions always occur at high temperatures, resulting in product mixtures. This process is therefore also particularly suitable for the preparation of heteroleptic complexes which can be employed as monomers in polymerisation reactions.
5. The process according to the invention enables the meridional complexes, which are otherwise only accessible in a complex manner and with very precise control of the reaction conditions, to be synthesised simply and selectively. Since the meridional isomer emits with a red shift compared with the facial isomer, it can preferably be used for the generation of red emission. The meridional complex can, if desired, also be converted selectively into the corresponding facial complex.

The present invention is explained in greater detail by the following examples, without wishing it to be restricted to the examples. It is possible for the person skilled in the art in the area of organic and organometallic synthesis to carry out the reactions according to the invention on further systems without further inventive step. In particular, the process can be carried out on differently substituted systems without further inventive step or also on systems which contain other aryl or heteroaryl groups instead of phenyl or pyridine or isoquinoline or benzopyrimidine.

EXAMPLES

The following syntheses are carried out under a protective-gas atmosphere, unless indicated otherwise. Iridium(III) chloride hydrate can be purchased from Heraeus and, according to iridium and water content determination, conforms to the formula $IrCl_3 * H_2O$. The simple substituted 2-phenylpyridines can be purchased from Aldrich or ABCR or prepared by standard literature procedures.

Comparative Example 1

Synthesis without Addition of Water 500 ml of dioxane are added to a mixture of 10 mmol of $IrCl_3*H_2O$, 60 mmol of 2-phenylpyridine and 300 mmol of sodium acetate, and the mixture is stirred at 80° C. for 30 h. The reaction does not proceed in homogeneous solution. A sediment of undefined composition forms. A tris-ortho-metallated metal complex cannot be isolated.

Comparative Example 2

Synthesis without Addition of Salt 500 ml of dioxane and 500 ml of water are added to a mixture of 10 mmol of $IrCl_3*H_2O$ and 60 mmol of 2-phenylpyridine, and the mixture is stirred at 80° C. for 30 h. After cooling, the precipitate is filtered off with suction. The dimeric chloro-bridged iridium complex, $[PhPy]_2IrCl_2Ir[PhPy]_2$, is obtained in a yield of about 90%.

Example 1

Synthesis of Homoleptic Meridional Metal Complexes from $IrCl_3*H_2O$—General Synthetic Procedure The organic solvent and water are added to a mixture of 10 mmol of $IrCl_3*H_2O$, 60 mmol of the ligand of the formula (5) and the salt, and the mixture is stirred at 80° C. for 30 h. The ligand structures, the salt, the solvents and the respective amounts are shown in Table 1 together with the yields. After cooling, the precipitate is filtered off with suction (P4), washed three times with 50 ml of a mixture of 50 ml of 1N aqueous hydrochloric acid and 150 ml of ethanol each time, three times with 50 ml of a mixture of 100 ml of water and 100 ml of ethanol each time and three times with 50 ml of ethanol each time and dried at 70° C. under reduced pressure. The purity of the products obtained by this process, without further purification, is at least 99.0% according to $^1$H-NMR.

TABLE 1

| Ex. | Ligand of formula (5) | Salt [mmol] | Solvent [ml] | Water [ml] | Product | Isomer | Yield [%] |
|---|---|---|---|---|---|---|---|
| 1a) | (pyridine-phenyl structure) | NaAc 300 | Dioxane 500 | 500 | (Ir complex, tris) | mer | 83.4 |
| 1b) | see Ex. 1a) | NaAc 300 | Dioxane 700 | 300 | see Ex. 1a) | mer | 86.0 |
| 1c) | see Ex. 1a) | NaAc 300 | Dioxane 600 | 400 | see Ex. 1a) | mer | 78.1 |
| 1d) | see Ex. 1a) | NaAc 100 | Dioxane 500 | 500 | see Ex. 1a) | mer | 82.9 |
| 1e) | see Ex. 1a) | NaAc 300 | 2-Ethoxyethanol 500 | 500 | see Ex. 1a) | mer | 74.9 |
| 1f) | see Ex. 1a) | NaAc 300 | THF 500 | 500 | see Ex. 1a) | mer | 71.5 |
| 1g) | see Ex. 1a) | KAc 300 | Dioxane 500 | 500 | see Ex. 1a) | mer | 85.4 |

TABLE 1-continued
| Ex. | Ligand of formula (5) | Salt [mmol] | Solvent [ml] | Water [ml] | Product | Isomer | Yield [%] |
|---|---|---|---|---|---|---|---|
| 1h) | see Ex. 1a) | NH₄Ac 300 | Dioxane 500 | 500 | see Ex. 1a) | mer | 87.1 |
| 1i) | see Ex. 1a) | Na benzoate 300 | Dioxane 500 | 500 | see Ex. 1a) | mer | 88.2 |
| 1j) | see Ex. 1a) | Na propionate 300 | Dioxane 500 | 500 | see Ex. 1a) | mer | 84.4 |
| 1k) | 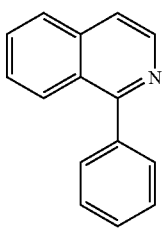 | NaAc 300 | Dioxane 500 | 500 | 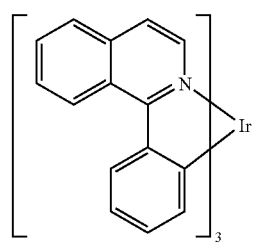 | mer | 91.6 |
| 1l) | 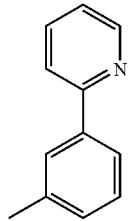 | NaAc 300 | Dioxane 500 | 500 | 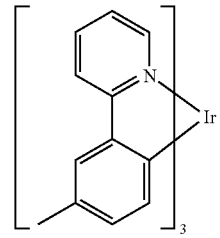 | mer | 89.8 |
| 1m) | 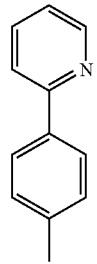 | NaAc 300 | Dioxane 500 | 500 | 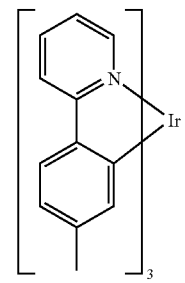 | mer | 77.5 |
| 1n) | 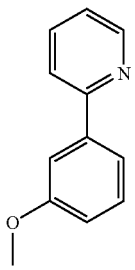 | NaAc 300 | Dioxane 500 | 500 | 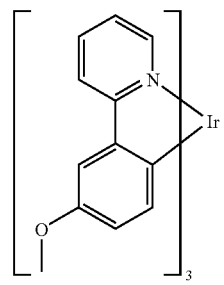 | mer | 85.8 |
| 1o) | 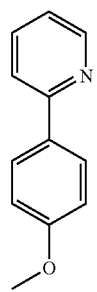 | NaAc 300 | Dioxane 500 | 500 | 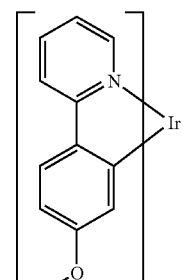 | mer | 78.6 |

TABLE 1-continued
| Ex. | Ligand of formula (5) | Salt [mmol] | Solvent [ml] | Water [ml] | Product | Isomer | Yield [%] |
|---|---|---|---|---|---|---|---|
| 1p) | 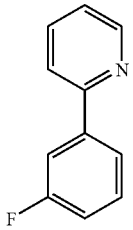 | NaAc 300 | Dioxane 500 | 500 | 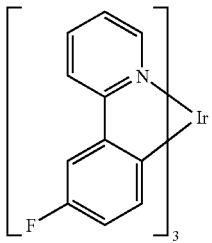 | mer | 82.4 |
| 1q) | 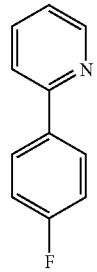 | NaAc 300 | Dioxane 500 | 500 | 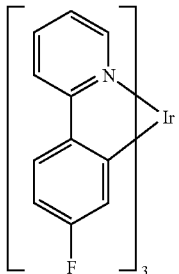 | mer | 76.7 |
| 1r) | 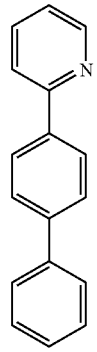 | NaAc 300 | Dioxane 700 | 300 | 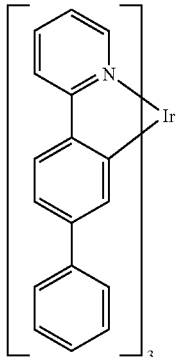 | mer | 85.5 |
| 1s) | 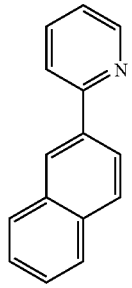 | NaAc 300 | Dioxane 700 | 300 | 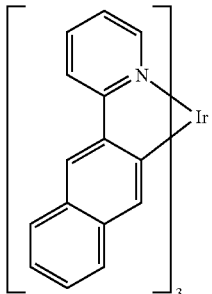 | mer | 88.0 |
| 1t) | 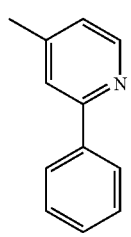 | NaAc 300 | Dioxane 500 | 500 | 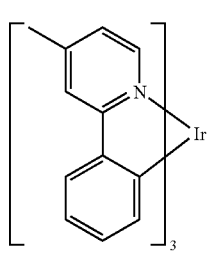 | mer | 75.0 |

TABLE 1-continued

| Ex. | Ligand of formula (5) | Salt [mmol] | Solvent [ml] | Water [ml] | Product | Isomer | Yield [%] |
|---|---|---|---|---|---|---|---|
| 1u) | 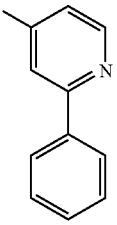 | NaAc 300 | Dioxane 500 | 500 | 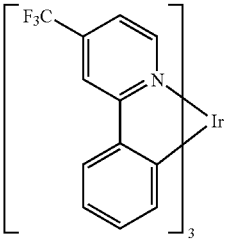 | mer | 91.4 |
| 1v) | 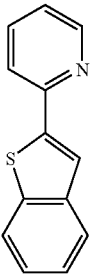 | NaAc 300 | Dioxane 500 | 500 | 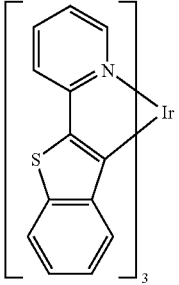 | mer | 81.2 |

Notes
NaAc = sodium acetate
KAc = potassium acetate
mer = meridional
Ex. 1f) reaction temperature 60° C.

Example 2

Synthesis of Homoleptic Facial Metal Complexes from IrCl$_3$*H$_2$O—General Synthetic Procedure The organic solvent and water are added to a mixture of 10 mmol of IrCl$_3$*H$_2$O, 300 mmol of the ligand of the formula (5) and the salt, and the mixture is stirred at 80° C. for 30 h. The ligand structures, the salt, the solvents and the respective amounts are shown in Table 2 together with the yields. After cooling, the precipitate is filtered off with suction (P4), washed three times with 50 ml of a mixture of 50 ml of 1N aqueous hydrochloric acid and 150 ml of ethanol each time, three times with 50 ml of a mixture of 100 ml of water and 100 ml of ethanol each time and three times with 50 ml of ethanol each time and dried at 70° C. under reduced pressure. The purity of the products obtained by this process, without further purification, is at least 99.0% according to $^1$H-NMR.

TABLE 2

| Ex. | Ligand of formula (5) | Salt [mmol] | Solvent [ml] | Water [ml] | Product | Isomer | Yield [%] |
|---|---|---|---|---|---|---|---|
| 2a) | 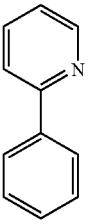 | Na$_2$SO$_4$ 300 | Dioxane 500 | 500 | 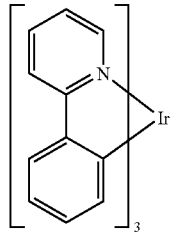 | fac | 88.0 |
| 2b) | see Ex. 2a) | NaHSO$_4$ 300 | Dioxane 500 | 500 | see Ex. 2a) | fac | 62.3 |
| 2c) | see Ex. 2a) | NH$_4$SO$_4$ 300 | Dioxane 500 | 500 | see Ex. 2a) | fac | 62.4 |
| 2d) | see Ex. 2a) | KH$_2$PO$_4$ 300 | Dioxane 500 | 500 | see Ex. 2a) | fac | 76.7 |
| 2e) | see Ex. 2a) | NaHCO$_3$ 300 | Dioxane 500 | 500 | see Ex. 2a) | fac | 79.7 |

TABLE 2-continued

| Ex. | Ligand of formula (5) | Salt [mmol] | Solvent [ml] | Water [ml] | Product | Isomer | Yield [%] |
|---|---|---|---|---|---|---|---|
| 2f) | (2-(m-tolyl)pyridine) | $KH_2PO_4$ 300 | Dioxane 500 | 500 | [Ir(methyl-phenylpyridine)$_3$] | fac | 83.1 |
| 2g) | (2-(3-fluorophenyl)pyridine) | $KH_2PO_4$ 300 | Dioxane 500 | 500 | [Ir(fluoro-phenylpyridine)$_3$] | fac | 74.1 |
| 2h) | (2-(3-methoxyphenyl)pyridine) | $KH_2PO_4$ 300 | Dioxane 500 | 500 | [Ir(methoxy-phenylpyridine)$_3$] | fac | 89.2 |

Notes
fac = facial

Example 3

Synthesis of Homoleptic Facial Metal Complexes From $IrCl_3*H_2O$ with Addition of Amino Acids/Aminosulfonic Acids—General Synthetic Procedure The organic solvent and water are added to a mixture of 10 mmol of $IrCl_3*H_2O$, 60 mmol of the ligand of the formula (5) and the amino acid or amino-sulfonic acid, and the mixture is stirred at 80° C. for 30 h. The ligand structures, the amino acid or aminosulfonic acid, the solvents and the respective amounts are shown in Table 3 together with the yields. After cooling, the precipitate is filtered off with suction (P4), washed three times with 50 ml of a mixture of 50 ml of 1N aqueous hydrochloric acid and 150 ml of ethanol each time, three times with 50 ml of a mixture of 100 ml of water and 100 ml of ethanol each time and three times with 50 ml of ethanol each time and dried at 70° C. under reduced pressure. The purity of the products obtained by this process, without further purification, is at least 99.0% according to $^1$H-NMR.

TABLE 3

| Ex. | Comp. of formula 5 | Aminoacid/ aminosulfonic acid [mmol] | Solvent [ml] | Water [ml] | Product | Isomer | Yield [%] |
|---|---|---|---|---|---|---|---|
| 3a) | (2-phenylpyridine) | Glycine 300 | Dioxane 500 | 500 | [Ir(phenylpyridine)$_3$] | fac | 91.3 |

TABLE 3-continued

| Ex. | Comp. of formula 5 | Aminoacid/ aminosulfonic acid [mmol] | Solvent [ml] | Water [ml] | Product | Isomer | Yield [%] |
|---|---|---|---|---|---|---|---|
| 3b) | see Ex. 3a) | Alanine 300 | Dioxane 500 | 500 | see Ex. 3a) | fac | 90.0 |
| 3c) | see Ex. 3a) | DMG 300 | Dioxane 500 | 500 | see Ex. 3a) | fac | 91.3 |
| 3d) | see Ex. 3a) | Glycine 100 | Dioxane 500 | 500 | see Ex. 3a) | fac | 88.6 |
| 3e) | see Ex. 3a) | Na-DMG 300 | Dioxane 500 | 500 | see Ex. 3a) | fac | 92.8 |
| 3f) | see Ex. 3a) | Na-DEG 300 | Dioxane 500 | 500 | see Ex. 3a) | fac | 92.6 |
| 3g) | see Ex. 3a) | DMAB 300 | Dioxane 500 | 500 | see Ex. 3a) | fac | 79.1 |
| 3h) | see Ex. 3a) | Taurine 300 | Dioxane 500 | 500 | see Ex. 3a) | fac | 85.9 |
| 3i) | 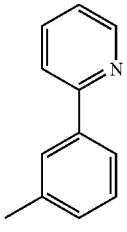 | DMG 300 | Dioxane 500 | 500 | 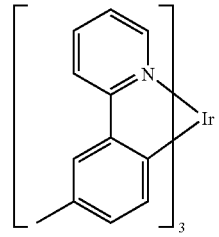 | fac | 86.1 |
| 3j) | 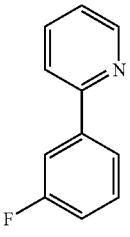 | DMG 300 | Dioxane 500 | 500 | 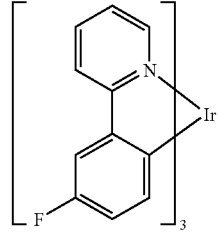 | fac | 82.1 |
| 3k) | 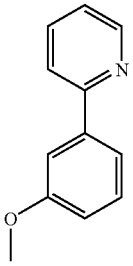 | DMG 300 | Dioxane 500 | 500 | 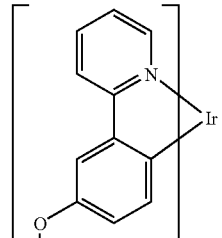 | fac | 88.0 |
| 3l) | 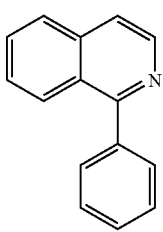 | DMG 300 | Dioxane 500 | 500 | 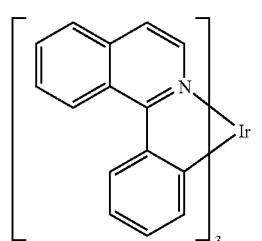 | fac | 82.7 |

TABLE 3-continued

| Ex. | Comp. of formula 5 | Aminoacid/ aminosulfonic acid [mmol] | Solvent [ml] | Water [ml] | Product | Isomer | Yield [%] |
|---|---|---|---|---|---|---|---|
| 3m) | 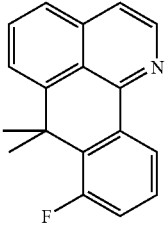 | DMG 300 | Dioxane 500 | 500 | 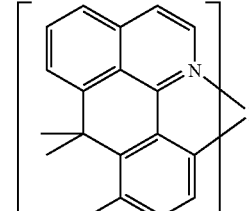 | fac | 89.6 |

Notes
DMG = N,N-dimethylglycine
Na-DMG = sodium N,N-dimethylglycinate
Na-DEG = sodium N,N-diethylglycinate
DMAB = 4-(N,N-dimethylamino)butyric acid
fac = facial

Example 4

Synthesis of Homoleptic Meridional and Heteroleptic Metal Complexes from Dimeric Iridium Complexes—General Synthetic Procedure 500 ml of dioxane and 500 ml of water are added to a mixture of 5 mmol of the dimeric iridium complex of the formula (4), 40 mmol of the ligand of the formula (5) and 300 mmol of sodium acetate, and the mixture is stirred at 80° C. for 30 h (Examples 4a) to 4f)). Alternatively, 50 ml of dioxane and 50 ml of water are added to a mixture of 0.5 mmol of the dimeric iridium complex of the formula (4), 6 mmol of the ligand of the formula (5) and 30 mmol of sodium acetate, and the mixture is stirred at 80° C. for 30 h (Examples 4 g) to 4t)). In each case, the corresponding meridional complexes are obtained. The precise structures of the starting complex and the ligand are shown in Table 4 together with the yields. After cooling, the precipitate is filtered off with suction (P4), washed three times with 50 ml of a mixture of 50 ml of 1N aqueous hydrochloric acid and 150 ml of ethanol each time, three times with 50 ml of a mixture of 100 ml of water and 100 ml of ethanol each time and three times with 50 ml of ethanol each time and dried at 70° C. under reduced pressure. The purity of the products obtained by this process, without further purification, is at least 99.0% according to $^1$H-NMR.

The dimeric iridium complexes of the formula (4) can be prepared as described in the literature (K. A. King, P. J. Spellane, R. J. Watts, *J. Am. Chem. Soc.* 1985, 107, 1431-1432), for example:

A suspension of 7,7-dimethyl-8-fluorodibenzo[de,h]quinoline (preparation as described in WO 05/033244) (4.0 g, 15.20 mmol, 2.1 eq.) and IrCl$_3$*H$_2$O (2.55 g, 7.24 mmol) in 120 ml of ethoxyethanol and 40 ml of water is stirred at 130° C. for 16 h under an inert-gas atmosphere. The precipitated solid is filtered off under a protective gas, washed with water (100 ml), MeOH (100 ml), diethyl ether (50 ml) and hexane (100 ml), giving 3.84 g (2.55 mmol) of an orange-red powder, corresponding to 70.6% of theory.

TABLE 4

| No. | Ligand of formula (5) | Iridium complex of formula (4) | Product | [%] |
|---|---|---|---|---|
| 4a) | 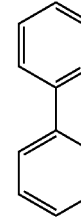 | 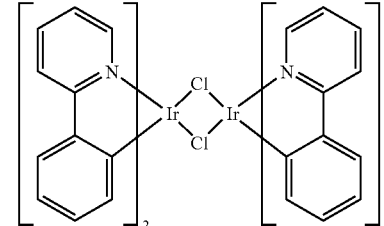 | 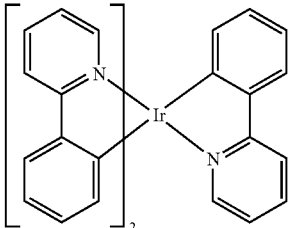 | 80.0 |
| 4b) | 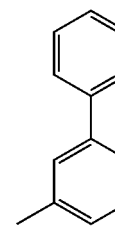 | 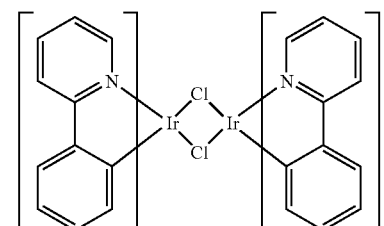 | 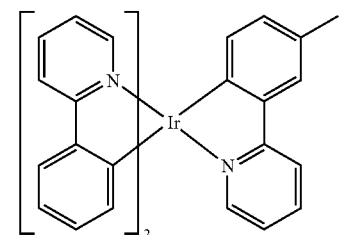 | 82.9 |

TABLE 4-continued

| No. | Ligand of formula (5) | Iridium complex of formula (4) | Product | [%] |
|---|---|---|---|---|
| 4c) | | | | 76.3 |
| 4d) | | | | 88.5 |
| 4e) | | | | 78.3 |
| 4f) | | | | 77.8 |
| 4g) | | | | 68.9 |
| 4h) | | | | 72.3 |

TABLE 4-continued

| No. | Ligand of formula (5) | Iridium complex of formula (4) | Product | [%] |
|---|---|---|---|---|
| 4i) | | | | 75.7 |
| 4j) | | | | 70.3 |
| 4k) | | | | 67.8 |
| 4l) | | | | 83.6 |
| 4m) | | | | 66.1 |
| 4n) | | | | 69.6 |
| 4o) | | | | 78.3 |

TABLE 4-continued

| No. | Ligand of formula (5) | Iridium complex of formula (4) | Product | [%] |
|---|---|---|---|---|
| 4p) | | | | 79.8 |
| 4q) | | | | 71.5 |
| 4r) | | | | 74.1 |
| 4s) | | | | 81.6 |
| 4t) | | | | 83.7 |

Example 5

Synthesis of Homoleptic Facial and Heteroleptic Iridium Complexes from Dimeric Iridium Compounds—General Synthetic Procedure 500 ml of dioxane and 500 ml of water are added to a mixture of 5 mmol of the dimeric iridium complex of the formula (4), 40 mmol of the ligand of the formula (5) and 300 mmol of N,N-dimethylglycine, and the mixture is stirred at 80° C. for 30 h. Alternatively, 50 ml of dioxane and 50 ml of water are added to a mixture of 0.5 mmol of the dimeric iridium complex of the formula (4), 6 mmol of the ligand of the formula (5) and 30 mmol of N,N-dimethylglycine, and the mixture is stirred at 80° C. for 30 h (Examples 5f to 5s)). The corresponding facial complexes are formed. The precise structures of the complex and the ligand are shown in Table 5 together with the yields. After cooling, the precipitate is filtered off with suction (P4), washed three times with 50 ml of a mixture of 50 ml of 1N aqueous hydrochloric acid and 150 ml of ethanol each time, three times with 50 ml of a mixture of 100 ml of water and 100 ml of ethanol each time and three times with 50 ml of ethanol each time and dried at 70° C. under reduced pressure. The purity of the products obtained by this process, without further purification, is at least 99.0% according to $^1$H-NMR.

TABLE 5

| Ex. | Ligand of formula (5) | Iridium complex of formula (4) | Product | [%] |
|---|---|---|---|---|
| 5a) | | | | 87.0 |
| 5b) | | | | 82.5 |
| 5c) | | | | 78.8 |
| 5d) | | | | 81.2 |
| 5e) | | | | 70.3 |
| 5f) | | | | 79.2 |
| 5g) | | | | 81.0 |

| Ex. | Ligand of formula (5) | Iridium complex of formula (4) | Product | [%] |
|---|---|---|---|---|
| 5h) | | | | 72.4 |
| 5i) | | | | 69.1 |
| 5j) | | | | 71.9 |
| 5k) | | | | 74.8 |
| 5l) | | | | 65.4 |
| 5m) | | | | 72.4 |
| 5n) | | | | 81.5 |

TABLE 5-continued

| Ex. | Ligand of formula (5) | Iridium complex of formula (4) | Product | [%] |
|---|---|---|---|---|
| 5o) | | | | 81.1 |
| 5p) | | | | 69.3 |
| 5q) | | | | 74.6 |
| 5r) | | | | 79.8 |
| 5s) | | | | 82.9 |

The invention claimed is:

1. A process for preparing metal complexes of formula (1)

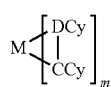

(1)

wherein

M is Rh, Ir, Pd, or Pt;

DCy is on each occurrence, identically or differently, a cyclic group optionally substituted with R and which comprises at least one neutral donor atom via which DCy is bonded to M;

CCy is on each occurrence, identically or differently, a cyclic group optionally substituted with R which comprises a carbon atom or a negatively charged nitrogen atom via which CCy is bonded to M;

wherein the bond between DCy and CCy is a covalent bond, and wherein DCy and CCy are optionally further connected to each other via a radical R;

R is on each occurrence, identically or differently, F, Cl, Br, I, $NO_2$, CN, $NH_2$, $NHR^1$, $N(R^1)_2$, $B(OH)_2$, $B(OR^1)_2$, CHO, COOH, $CONH_2$, $CON(R^1)_2$, $SO_3H$, $C(=O)R^1$, $P(=O)(R^1)_2$, $S(=O)R^1$, $S(=O)_2R^1$, $P(R^1)_3^+$, $N(R^1)_3^+$, OH, SH, a straight-chain alkyl or alkoxy group having up to 20 C atoms or a branched or cyclic alkyl or alkoxy group having 3 to 20 C atoms, each optionally substituted by one or more groups $R^2$, wherein in each instance one or more non-adjacent CH$_2$ groups are optionally replaced by —O—, —S—, —NR$^1$—, —CONR$^1$—, —CO—O—, —CR$^1$=CR$^1$— or —C≡C—, an aromatic or heteroaromatic ring system having 5 to 30 aromatic ring atoms, optionally substituted by one or more radicals R$^2$, or an aryloxy, heteroaryloxy, arylamino, or heteroarylamino group having 5 to 30 aromatic ring atoms, optionally substituted by one or more radicals R$^2$; wherein two or more substituents R, either on the same ring or on the two different rings, optionally define a further mono- or polycyclic, aliphatic or aromatic ring system with one another or with R$^1$, R$^2$, and/or R$^3$;

R$^1$ is on each occurrence, identically or differently, H, a straight-chain alkyl group having up to 20 C atoms or a branched or cyclic alkyl group having 3 to 20 C atoms, each optionally substituted by one or more groups R$^2$, wherein in each instance one or more non-adjacent CH$_2$ groups which are not bonded directly to a heteroatom are optionally replaced by —O—, —S—, —NR$^3$—, —CONR$^3$—, —CO—O—, —CR$^3$=CR$^3$— or —C≡C—, or an aromatic or heteroaromatic ring system having 5 to 30 aromatic ring atoms, optionally substituted by one or more radicals R$^3$; and wherein two or more substituents R$^1$ optionally define a further mono- or polycyclic, aliphatic or aromatic ring system with one another or with R, R$^2$, and/or R$^3$;

R$^2$ is on each occurrence, identically or differently, H, F, Cl, Br, I, NO$_2$, CN, NH$_2$, NHR$^3$, N(R$^3$)$_2$, B(OH)$_2$, B(OR$^3$)$_2$, CHO, COOH, CON(R$^3$)$_2$, SO$_3$H, C(=O)R$^1$, P(=O)(R$^1$)$_2$, S(=O)R$^1$, S(=O)$_2$R$^1$, P(R$^3$)$_3$$^+$, N(R$^3$)$_3$$^+$, OH, SH, a straight-chain alkyl or alkoxy group having up to 20 C atoms or a branched or cyclic alkyl or alkoxy group having 3 to 20 C atoms, each optionally substituted by one or more groups R$^3$, wherein in each instance one or more non-adjacent CH$_2$ groups are optionally replaced by —O—, —S—, —NR$^3$—, —CONR$^3$—, —CO—O—, —CR$^3$=CR$^3$— or —C≡C—, or an aromatic or heteroaromatic ring system having 5 to 30 aromatic ring atoms, optionally substituted by one or more radicals R$^3$, or an aryloxy, heteroaryloxy, arylamino, or heteroarylamino group having 5 to 30 aromatic ring atoms, optionally substituted by one or more radicals R$^3$; wherein two or more substituents R$^2$, either on the same ring or on the two different rings, optionally define a further mono- or polycyclic, aliphatic or aromatic ring system with one another or with R, R$^1$, and/or R$^3$;

R$^3$ is, identically or differently on each occurrence, H or an aliphatic or aromatic hydrocarbon radical having up to 20 C atoms, wherein two or more radicals R$^3$ optionally define a ring system with one another;

m is 2 when M is Pd or Pt and is 3 when M is Rh or Ir;

comprising reacting a metal compound of formula (2), (3), or (4)

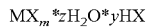  Formula (2)

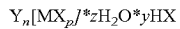  Formula (3)

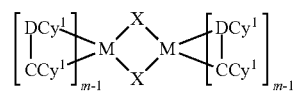  Formula (4)

wherein M and m are as defined above, and wherein

X is on each occurrence, identically or differently, F, Cl, Br, or I;

Y is on each occurrence, identically or differently, an alkali metal cation, an alkaline earth metal cation, an ammonium cation, a tetraalkylammonium cation having 4 to 40 C atoms, or a tetraalkylphosphonium cation having 4 to 40 C atoms;

p is 4 when M is Pd or Pt and is 6 when M is Rh or Ir;

n is the charge of M for a monovalent cation Y and is half the charge of M for a divalent cation Y;

z is an integer from 0 to 100;

y is an integer from 0 to 100;

with a compound of formula (5)

wherein DCy and CCy are as defined above; and wherein said reaction is carried out (1) in the presence of a salt whose anion contains at least two oxygen atoms and (2) in a solvent mixture comprising at least one organic solvent and at least 2% by volume of water wherein said salt is an alkali metal, alkaline earth metal, ammonium, tetraalkylammonium, tetraalkylphosphonium, and/or tetraarylphosphonium salt of carbonate, hydrogencarbonate, sulfate, hydrogensulfate, sulfite, hydrogensulfite, nitrate, nitrite, phosphate, hydrogenphosphate, dihydrogenphosphate, or borate; an alkali metal, alkaline earth metal, ammonium, tetraalkylammonium, tetraalkylphosphonium, and/or tetraarylphosphonium salt of organic carboxylic acids having up to 20 C atoms, organic sulfonic acids having up to 20 C atoms, α-ketocarboxylates, β-ketoketonates, β-ketocarboxylates; salts of pyrocatechol and salicylic acid; an aminocarboxylic acid; an aromatic aminocarboxylic acid; an polyaminocarboxylic acid; an N-alkylated aminocarboxylic acid, wherein said alkyl groups contain up to 10 C atoms; an aminosulfonic acid or N-alkylated aminosulfonic acid, wherein said alkyl groups contain up to 10 C atoms; or salts of these compounds which are obtained by abstraction of one or more protons.

2. The process of claim 1, wherein a compound of formula (2) or a compound of formula (3) is reacted with a compound of formula (5) to give a homoleptic metal complex, or a compound of formula (4) is reacted with a compound of formula (5) of the same type to give a homoleptic metal complex, or a compound of formula (4) is reacted with a compound of formula (5) of a different type to give a heteroleptic metal complex.

3. The process of claim 1, wherein, for metal compounds of formula (2), y is an integer from 0 to 10 and z is an integer from 1 to 10 and, for metal compounds of formula (3), both y and z are integers from 0 to 10.

4. The process of claim 1, wherein X, identically or differently on each occurrence, is Cl or Br.

5. The process of claim 4, wherein X is Cl.

6. The process of claim 1, wherein

CCy identically or differently on each occurrence, is an aromatic or heteroaromatic group which has 5 to 20 aromatic ring atoms optionally substituted with one or more R and which is bonded to M via a carbon atom; and DCy identically or differently on each occurrence, is a cyclic group having 5 to 20 ring atoms, which comprises a neutral nitrogen atom as donor atom, wherein said neutral nitrogen is bonded in an imine functionality or is part of a heteroaromatic system.

7. The process of claim 1, wherein said salt is an organic salt or an inorganic salt or a zwitterionic compound.

8. The process of claim 1, wherein said at least two oxygen atoms are bonded in said salt in a 1,3-, a 1,4- or a 1,5-arrangement.

9. The process of claim 1, wherein the molar ratio of M to salt is in the range of from 1:1 to 1:1000.

10. The process of claim 1, wherein the reaction is carried out in a homogeneous solution.

11. The process of claim 1, wherein said at least one organic solvent is a polar protic solvent, a polar aprotic solvent, or a mixture thereof.

12. The process of claim 1, wherein said at least one organic solvent is an alcohol, a diol, a polyalcohol, an alkoxyalcohol, a water-miscible open-chain or cyclic ether, DMSO, NMP, DMF, or mixtures thereof.

13. The process of claim 12, wherein said alcohol has up to 5 C atoms.

14. The process of claim 1, wherein the proportion of water in said solvent mixture is in the range of from 5 to 90% by volume.

15. The process of claim 1, wherein the concentration of the compound of formula (2) or formula (3) is in the range of from 0.5 mmol/l to 100 mmol/l, and the concentration of the compound of formula (4) is in the range of from 1 to 1000 mmol/l.

16. The process of claim 1, wherein M is Ir; the molar ratio of the compound of formula (2) or formula (3) to the compound of formula (5) is in the range of from 1:1 to 1:60; and the molar ratio of the compound of formula (4) to the compound of formula (5) is in the range of from 1:1 to 1:100.

17. The process of claim 1, further comprising a reaction step for converting the meridional complex of formula (1) into a facial tris-ortho-metallated metal complex.

* * * * *